United States Patent [19]

Pez

[11] 4,200,716

[45] Apr. 29, 1980

[54] PROCESS FOR POLYMERIZING ACETYLENE

[75] Inventor: Guido Pez, Boonton, N.J.

[73] Assignee: Allied Chemical Corporation, Morris Township, Morris County, N.J.

[21] Appl. No.: 957,592

[22] Filed: Nov. 3, 1978

[51] Int. Cl.$^2$ .......................... C08F 4/48; C08F 38/02
[52] U.S. Cl. .................................. 526/141; 526/142; 526/160; 526/170; 526/285
[58] Field of Search ............... 526/141, 142, 160, 170, 526/285

[56] References Cited

U.S. PATENT DOCUMENTS

| Re. 29,368 | 8/1977 | Pez. | |
|---|---|---|---|
| 2,886,579 | 5/1959 | Herman | 526/170 |
| 2,963,471 | 12/1960 | Herman | 526/170 |
| 3,776,932 | 12/1973 | Pez. | |
| 4,024,169 | 5/1977 | Pez. | |

OTHER PUBLICATIONS

J. Am. Chem. Soc. 100, pp. 1015–1017, (1978).
J. Poly. Sci., Polymer Chemistry 12, pp. 11–20 (1974).
Chem. Abs. 76, p. 15005, (1972).
Chem. Abs., 73, p. 67036S (1970).
Bull. Chem. Soc., Japan 38, p. 859 (1965).
J. Am. Chem. Soc. 92, pp. 6182–6185 (1970).
J. Am. Chem. Soc. 76 pp. 8072–8078 (1976).
J. Chem. Phys. 68 (12) pp. 5405–5409 (1978).
J. Chem. Phys. 69(1, pp. 106–111 (1978).

*Primary Examiner*—Harry Wong, Jr.
*Attorney, Agent, or Firm*—Robert J. North; Robert A. Harman

[57] ABSTRACT

A process is described for polymerizing acetylene to selectively produce partially crystalline polyacetylene in its cis and trans configurations, which when doped with halogen additives, are useful as electrical conductors or semi-conductors. The polymerization is conducted in a solution containing a lithium dicyclopentadienyl titanium hydride catalyst in a liquid organic solvent therefor, at a temperature in the range of about $-120°$ to $+250°$ C. Lower process temperatures, such as below $-60°$ C., favor the formation of the cis form, and higher temperatures, above $0°$ C., favor the formation of the trans form.

10 Claims, No Drawings

PROCESS FOR POLYMERIZING ACETYLENE

BACKGROUND OF THE INVENTION

1. Field of the Invention.

This invention relates to a novel method for polymerizing acetylene utilizing a lithium dicyclopentadienyl titanium hydride catalyst.

2. Brief Description of the Prior Art

Partially crystalline forms of polyacetylene, in the cis or trans configurations, when doped with controlled amounts of an electron-attracting species such as a halogencontaining compound, specifically iodine or arsenic trifluoride, are known to exhibit increases in conductivity over a remarkably wide range of up to about 11 magnitudes. See *J. Am. Chem. Soc. Vol.* 100, pp. 1015–1017 (1978). The "doped" polymers are capable of functioning as electrical conductors or semi-conductors.

Catalytic methods for synthesizing polyacetylene in its respective cis and trans configurations, are well known in the art and include the use of Ziegler-type catalysts, described for example in *J. Poly. Sci. Polymer Chemistry, Ed. Vol.* 12, 11–20 (1974); the use of copper-aluminum-spinel solids, as described in *Kinet. Katal.* 12 (4), p. 974 (1971), *Chem. Abstracts*, 76, 15005 (1972); and the use of dicyclopentadienyl vanadium as described in Japanese Pat. No. 70 08,980 (1970), *Chem. Abstracts*, 73 67036s (1970).

The reference, *Bull Chem. Soc. Japan, Vol.* 38, 859 (1965), describes a method for polymerizing acetylene which involves a "titanocene"-type catalyst. However, subsequent work described in *J. Am. Chem. Soc., Vol.* 92, pp. 6182–6185 (1970), disclosed that the above "titanocene" material, as prepared by the reduction of dicyclopentadienyltitanium dichloride with sodium amalgam, actually used as a catalyst is in fact a dimer of cyclopentadienyl fulvalene titanium hydride.

The references of Guido Pez in *J. Am. Chem. Soc.* 98, 8070 (1976), U.S. Pat. No. 3,776,932 (1973), U.S. Pat. No. Re. 29,368 (1977) and U.S. Pat. No. 4,024,169 (1977), Allied Chemical being the assignee, disclose novel cyclopentadienyl titanium compounds useful in removing gaseous nitrogen from admixture with argon.

U.S. Application Ser. No. 957,392, filed Nov. 3, 1978 (assigned to Allied Chemical) by Guido Pez describes novel lithium dicyclopentadienyl titanium hydride compounds which are useful as catalysts in the dimerization of ethylene to 1-butene. However, no mention or suggestion is made in the above-described reference as to the use of lithium dicyclopentadienyl titanium hydride compositions as catalysts in the polymerization of acetylene.

There is a continuing need in the art for new, inexpensive and conveniently prepared compositions which can function as catalysts to efficiently polymerize acetylene into its respective cis and trans forms.

SUMMARY OF THE INVENTION

We have unexpectedly found that lithium dicyclopentadienyl titanium hydrides are excellent catalysts for carrying out the polymerization of acetylene to produce partially crystalline polyacetylene, in the cis or trans forms, which are useful as electrical conductors or semi-conductors when "doped" with certain halogen-containing additives.

In accordance with this invention there is provided a process for producing polyacetylene comprising contacting acetylene with a solution comprised of a liquid inert organic solvent and a lithium dicyclopentadienyl titanium hydride catalyst, of the formula, LiRR'TiH, wherein R and R' are cyclopentadienyl rings, of the empirical formula, $C_5H_5$, wherein the ring hydrogens may be independently substituted with a one or more groups inert toward lithium metal, said rings being bonded to titanium by sigma-bonds, pi-bonds or mixtures thereof, and said catalyst exhibiting a $^{13}C$ nuclear magnetic resonance spectrum in deuterated benzene in which observed values for the chemical shifts of the ring carbons in R are different from the observed values for ring carbon atoms in R', and said catalyst exhibiting an infrared spectrum in deuterated n-hexadecane in which a titanium metal-hydride absorption band is observed in the region of about 1250–1450 cm$^{-1}$, at a temperature at about $-120°$ to $+200°$ C., under a pressure of about 0.01 to 10 atmospheres, in the absence of elemental oxygen and water.

DESCRIPTION OF THE INVENTION AND PREFERRED EMBODIMENTS

The novelty of this invention process resides in the discovery that a novel class of catalyst compositions, the lithium dicyclopentadienyl titanium hydrides, developed by Guido Pez (assigned to Allied Chemical) and described in U.S. Application Ser. No. 957,392 filed Nov. 3, 1978. hereby incorporated by reference, are useful in polymerizing acetylene to selectively produce partially crystalline cis or trans forms of polyacetylene.

A full description of the catalyst composition, its physical properties, structure, and methods of synthesis are fully and adequately described in the above-identified incorporated reference, and need not be reiterated herein. Throughout this disclosure, by the term "catalyst", is meant the above-mentioned lithium cyclopentadienyl titanium hydride compositions. A preferred composition in the process is where both cyclopentadienyl rings are unsubstituted, and the molecule is represented by the formula:

Li($\eta$-$C_5H_5$)($C_5H_5$)Ti-H.

The invention process, in general, comprises dissolving the catalyst in a stirred inert organic solvent therefor, optionally containing a lithium cation chelating agent to aid in the solubility of the catalyst in the solvent. The solvent in the process must be anhydrous and free of elemental oxygen. Acetylene is then introduced into the system to contact the solution, or being bubbled therein thereby being absorbed. The polymerization is initiated and proceeds upon the absorption of acetylene under good agitation. The polymerization is allowed to proceed for a period until the desired amount of actylene is absorbed as indicated by a measureable decrease in the reaction pressure. The solvent is then distilled off under reduced pressure and the resulting black residue, being the crude polyacetylene, can be purified by washing with a suitable solvent. The process must be conducted under conditions rigorously excluding the presence of elemental oxygen and water. Conducting the process at temperatures from about $-110°$ to $-60°$ C., favors the formation of the cis configuration of polyacetylene and higher temperatures, from about $0°$ to $+250°$ C., favors the formation of the trans configuration.

The above-mentioned cis and trans "forms" of partially crystalline polyacetylene are known in the art, and are described in the aforementioned references, particularly the J. Poly. Sci. reference. They are normally black in color as bulk solids, or red, yellow or silvery in appearance as films, due to the extended conjugation of the unsaturated polymer chains, which are randomly oriented as evidenced by the fact that changes in the angle of incidence do not result in changes in the X-ray diffraction pattern, and can be conveniently distinguished from one another on the basis of their infrared spectra. Specifically, the cis form exhibits a characteristic C-H out-of-plane deformation band at 740 cm$^{-1}$, while the trans form exhibits a characteristic C-H out-of-plane deformation band at 1015 cm$^{-1}$. Mixtures of cis and trans forms can be estimated as to their relative weight percentages in a mixture of the two by comparing the relative amplitudes of the respective deformation bands of each form relative to known standards, by the method described in the above-mentioned reference.

By the term "cis" form, as used herein, is meant that the partially crystalline polyacetylene obtained in the process contains at least about 70 wt.% of the polyacetylene in the cis configuration, the remainder being the trans form. By the term "trans" form, as used herein, is meant that the partially crystalline polyacetylene, obtained in the process, contains at least about 70 wt. % of the polyacetylene in the trans configuration. The physical properties of the cis and trans forms are adequately described in the above-identified reference of *J. Poly. Sci, Poly. Chem. Ed. Vol.* 12, pp. 11–20 (1974), hereby incorporated by reference, and for the sake of brevity need not be reiterated herein.

By the term "crystalline polyacetylene", as used herein, is meant that the obtained polyacetylene exhibits an intense and sharp reflection at a Bragg angle ($2\theta$) of 23° to 24°, corresponding to an inner planar spacing of 3.8–3.5 angstroms as described by a K-alpha X-radiation, and does not exhibit amorphous scattering.

The inert liquid organic solvent used in the process must be anhydrous, free of elemental oxygen, and must be a suitable solvent for acetylene and for the lithium dicyclopentadienyl titanium hydride catalyst at the temperature of the polymerization.

Representative classes of suitable solvents useful in the process include $C_6$-$C_{14}$ aromatic hydrocarbons, $C_5$-$C_{18}$ linear or branched acyclic or cyclic saturated aliphatic hydrocarbons, $C_4$-$C_6$ cyclic saturated aliphatic mono- or diethers, $C_2$-$C_6$ linear or branched acyclic saturated aliphatic mono-or diethers, $C_7$-$C_{10}$ aromatic mono- or diethers, $C_3$-$C_8$ linear or branched saturated aliphatic tertiary amines, $C_5$-$C_8$ cyclic mono-olefins, $C_4$-$C_{12}$ linear or branched acyclic alpha-olefins, or mixtures thereof.

Representative examples of specific solvents include toluene, hexane, benzene, tetrahydrofuran, dioxane, diethyl ether, 1,2-dimethoxyethane, anisole, n-hexadecane, cyclohexane, triethylamine, cyclohexene, hexene, and the like, or mixtures thereof.

Amount of solvent used in the process is generally about 1,000 to 10,000 parts by weight per part of catalyst. However, the amount of solvent is not critical and larger or smaller amounts may be used as long as sufficient solvent is present used to dissolve a sufficient amount of catalyst and acetylene and to initiate and maintain the polymerization reaction.

In cases where the lithium dicyclopentadienyl titanium hydride catalyst is only sparingly soluble in the solvent, such as the saturated aliphatic hydrocarbons, described above, a lithium cation chelating agent may optionally be used to increase the solubility. Suitable chelating agents include tertiary amines such as N,N,N',N'-tetramethylethylenediamine, cyclic ethers such as 15-crown-5 and 18-crown-6, and cryptates, being bicyclic bridgehead nitrogen diamines, having oxymethylene bridges. Preferred chelating agent is N,N,N',N'-tetramethylethylenediamine.

The amount of said chelating agent used is that amount sufficient to completely dissolve the catalyst in the solvent used and may be as much as two moles chelating agent per mole of catalyst employed.

The amount of catalyst used in the process is not critical and various amounts may be used as desired, with the proviso that the yield of polyacetylene obtained is a function of the "catalyst turnover number," being defined as the number of grams of polyacetylene produced per gram of catalyst present. The catalysts turnover number will generally be in the range of about 50 to 100, and will be slightly affected by modifications in the reaction conditions. In general, about 1 part catalyst per 1000 to 10,000 parts by weight of solvent, are employed in the process, although higher and lower amounts being also effective and operative.

Acetylene is the limiting reagent in the process and the amount used is generally measured in terms of pressure, convertible to moles by the ideal gas equation, at the start of the polymerization and is generally in the range of about 1 to 5 atmospheres, assuming an atmosphere consisting essentially of acetylene or its molar equivalent at reduced pressure. The amount of acetylene used is dependent upon the size of the apparatus and other factors, and the total calculated amount of acetylene, used in the reaction, can be present at the beginning of the reaction or can be continuously monitored into the reaction solution during the process. Various grades of acetylene can be used, commercial, technical, etc., with the proviso that air and moisture and contaminant acetone are vigorously excluded from the acetylene feed stream prior to introduction into the reaction solution. The acetylene can be added at a temperature from about −80° to +250° C. and is preferably added at room temperature.

The contacting of the mixture of the dissolved catalyst and solvent with acetylene is generally accomplished by contact of an atmosphere of gaseous acetylene with the surface of the mixture. Upon contact, the acetylene is absorbed, dissolves in the mixture and undergoes polymerization in the presence of the catalyst. The "atmosphere" of acetylene can be substantially all acetylene, or can be a mixture of acetylene and an inert gas, such as argon. However, sufficient acetylene must be present to initiate and maintain the polymerization process.

The process can be conducted in the temperature range of about −120° C. to +200° C. Preferred temperature range for producing mainly the cis form is from about −110° to −60° C., and particularly preferred is the range from about −90° to −80° C. Preferred temperature range for producing mainly the trans form is from about 60° to about 200° C., and particularly preferred is the temperature range from about 80–100° C. Process temperatures between these preferred ranges lead to mixtures of cis and trans forms, in various weight ratios. In general, due to the greater stability of the trans form, and the tendency of the cis form to undergo isomerization, obtained polyacetylene mainly in the cis form will always contain some of the trans isomer unless the process is conducted at −90° C. and below.

The process can be conducted under a pressure from about 1 to 10 atmospheres or under a reduced pressure below atmospheric down to about 0.01 atmosphere with the proviso that sufficient pressure is present to aid in the absorption of acetylene by the reaction medium. Preferred pressure in the process is about one atmosphere.

The process must be conducted under conditions vigorously excluding elemental oxygen and water. Any conventional type of apparatus meeting these requirements can be used. The inventor utilized an evacuable glass apparatus on a laboratory scale as a means for excluding air and moisture, inlet means for introducing acetylene, and mechanical stirrer means for stirring and heating and Dewar flasks, containing dry ice-acetone mixtures as external means for cooling the reaction mixture. Commercial scale-up units useful on a plant scale can also be utilized, meeting these requirements, and will be obvious to one skilled in the art.

Yields of polyacetylene in the process are generally in the range of about 30 to 100 parts of polymer per part by weight of catalyst. The obtained polyacetylene can be readily isolated by filtration and purified by working with a suitable reaction-solvent described herein.

Modification and variations of the invention process will be obvious to one skilled in the art from the disclosure herein.

The following examples are illustrative of the best mode of carrying out the invention as contemplated by us should not be construed as being limitations on the scope or spirit of the invention.

EXAMPLE 1

Thirty mg. of crude lithium titanocene hydride (as obtained from reaction of lithium with dicyclopentadienyl titanium dichloride in ether described in U.S. Application No. 957,392, filed Nov. 3, 1978, by Guido Pez (assigned to Allied Chemical), hereby incorporated by reference, were dissolved in 250 ml of pure tetrahydrofuran, in the absence of elemental oxygen and water. The solution was stirred and cooled to −80° C. and the solution covered with an atmosphere of 2 liters of acetylene under a pressure of about one atmosphere. Polymerization began almost immediately upon absorption of acetylene by the stirred solution. The solution was continuously stirred and maintained at −80° C. for 1 hour, then warmed to −35° C. over a 3 to 4 hour period, and then allowed to warm slowly overnight under continuous stirring. The solvent was removed and the resulting polyacetylene was recovered as black shiny lumps in a yield of about 1 to 1.5 grams. Infrared spectral analysis showed the material to be mainly cis-polyacetylene, as evidenced by characteristic absorption band observed at about 740 cm$^{-1}$.

EXAMPLE 2

The procedure of Example 1 was repeated except that the catalyst (30 mg.) was first dissolved in N,N,N',N'-tetramethylethylenediamine to form a chelate and then excess amine was removed by vacuum distillation. Toluene (500 ml.) was added and the solution was covered with an atmosphere of acetylene (2 liters) at one atmosphere of pressure. The polymerization was carried out at a temperature of about 23–25° C., under agitation, until the uptake of acetylene gas was neglible as evidenced by a constant reaction pressure. Three grams of product were obtained which consisted mainly of the trans form of polyacetylene, as evidenced by the characteristic absorption band observed at about 1015 cm$^{-1}$.

I claim:

1. A process for producing polyacetylene comprising contacting acetylene with a solution comprised of a liquid inert organic solvent and a lithium dicyclopentadienyl titanium hydride catalyst of the formula, LiRR'TiH, wherein R and R' are cyclopentadienyl rings, of the empirical formula, $C_5H_5$, wherein the ring hydrogens may be independently substituted with one or more groups inert toward lithium metal, said rings being bonded to titanium by sigma-bonds, pi-bonds or mixtures thereof, and said catalyst exhibiting a $^{13}C$ nuclear magnetic resonance spectrum in deuterated benzene in which observed values for the chemical shifts of the ring carbons in R are different from the observed values for ring carbon atoms in R', and said catalyst exhibiting an infrared spectrum in deuterated n-hexadecane in which a titanium metal-hydride absorption band is observed in the region of about 1250–1450 cm$^{-1}$, at a temperature at about −120° to +200° C., under a pressure of about 0.01 to 10 atmospheres, in the absence of elemental oxygen and water.

2. The process of claim 1 wherein R and R' of said catalyst are both unsubstituted cyclopentadienyl rings, said catalyst having the formula, Li ($\eta$-$C_5H_5$) ($C_5H_5$) TiH.

3. the process of claim 1 wherein said temperature is about 60° to 200° C. and the resulting polyacetylene is substantially in the trans configuration.

4. The process of claim 1 wherein said temperature is about −110° to −60° C. and the resulting polyacetylene is substantially in the cis configuration.

5. The process of claim 1 conducted at about 1 atmosphere of pressure.

6. The process of claim 1 wherein said solvent is a $C_6$-$C_{14}$ aromatic hydrocarbon, $C_5$-$C_{18}$ linear or branched acyclic or cyclic saturated aliphatic hydrocarbon, $C_4$-$C_6$ saturated aliphatic cyclic mono- or diether, $C_2$-$C_6$ linear or branched acyclic saturated aliphatic mono- or diether, $C_7$-$C_{10}$ aromatic mono- or diether, $C_3$-$C_8$ linear or branched saturated aliphatic tertiary amine, $C_4$-$C_{12}$ cyclic monoolefin, $C_5$-$C_8$ linear or branched acyclic alpha-olefin, or mixtures thereof.

7. The process of claim 6 wherein said solvent is toluene, hexane, benzene, tetrahydrofuran, dioxane, diethyl ether, 1,2-dimethoxyethane, anisole, n-hexadecane, cyclohexane, triethylamine, cyclohexene, hexene, or mixtures thereof.

8. the process of claim 1 wherein said solution is further comprised of a chelating agent for lithium cation.

9. The process of claim 8 wherein said chelating agent is N,N,N',N'-tetramethylethylenediamine.

10. The process of claim 1 wherein said catalyst is present in an amount of about 1 part catalyst per 1000 to 10,000 parts by weight solvent.

* * * * *